United States Patent
Fotinos et al.

(10) Patent No.: US 11,052,054 B2
(45) Date of Patent: Jul. 6, 2021

(54) METHOD FOR MANUFACTURING A TRANSDERMAL DEVICE

(71) Applicant: INEP EUROPE SARL, Luxembourg (LU)

(72) Inventors: Spiros Fotinos, Attika (GR); Jerome Langlume, Paris (FR); Jean Paul Caravita, Paris (FR)

( * ) Notice: Subject to any disclaimer, the term of this patent is extended or adjusted under 35 U.S.C. 154(b) by 0 days.

(21) Appl. No.: 15/491,419

(22) Filed: Apr. 19, 2017

(65) Prior Publication Data

US 2018/0303762 A1    Oct. 25, 2018

(51) Int. Cl.
*A61K 9/70* (2006.01)
*A61F 13/02* (2006.01)

(52) U.S. Cl.
CPC .......... *A61K 9/703* (2013.01); *A61F 13/0289* (2013.01); *A61K 9/7084* (2013.01); *A61F 2013/0296* (2013.01)

(58) Field of Classification Search
None
See application file for complete search history.

(56) References Cited

U.S. PATENT DOCUMENTS

| 4,588,580 | A | 5/1986 | Gale et al. |
| 6,365,178 | B1 | 4/2002 | Venkateshwaran et al. |
| 7,247,315 | B2 | 7/2007 | Brown et al. |
| 2001/0033858 | A1 | 10/2001 | Zhang |
| 2008/0202675 | A1* | 8/2008 | Sever ............ B32B 37/025 156/238 |
| 2009/0238861 | A1 | 9/2009 | Miller |
| 2014/0276478 | A1 | 9/2014 | Liao et al. |
| 2017/0189534 | A1* | 7/2017 | Lee ............ A61K 9/7053 |
| 2017/0291020 | A1* | 10/2017 | Tolia ............ A61M 35/00 |

FOREIGN PATENT DOCUMENTS

WO    2016149077 A2    9/2016

OTHER PUBLICATIONS

International Search Report, PCT/US18/26802, dated Jul. 2, 2018.

* cited by examiner

*Primary Examiner* — David J Blanchard
*Assistant Examiner* — Daniel F. Coughlin
(74) *Attorney, Agent, or Firm* — Porzio Bromberg & Newman P.C.

(57) ABSTRACT

The invention relates to a method for manufacturing a transdermal patch from a drug-containing web that minimizes waste. The web is a layered composite that includes at least a backing layer and a drug-in-adhesive layer and a first strippable release liner. The web is kiss-cut along intersecting cut lines at least down to the depth of the liner, generally defining the extent of individual transdermal patches. The intersections of the cut lines define small zones that are punched out of the web in a generally star shape. The portions of the web above the liner are peeled away from the liner and transferred to a faster moving second liner so that the patches are now further spaced apart from one another. This second liner is then cut to provide transdermal patches that are mounted to release liners that are substantially broader in extent than the patches themselves.

7 Claims, 1 Drawing Sheet

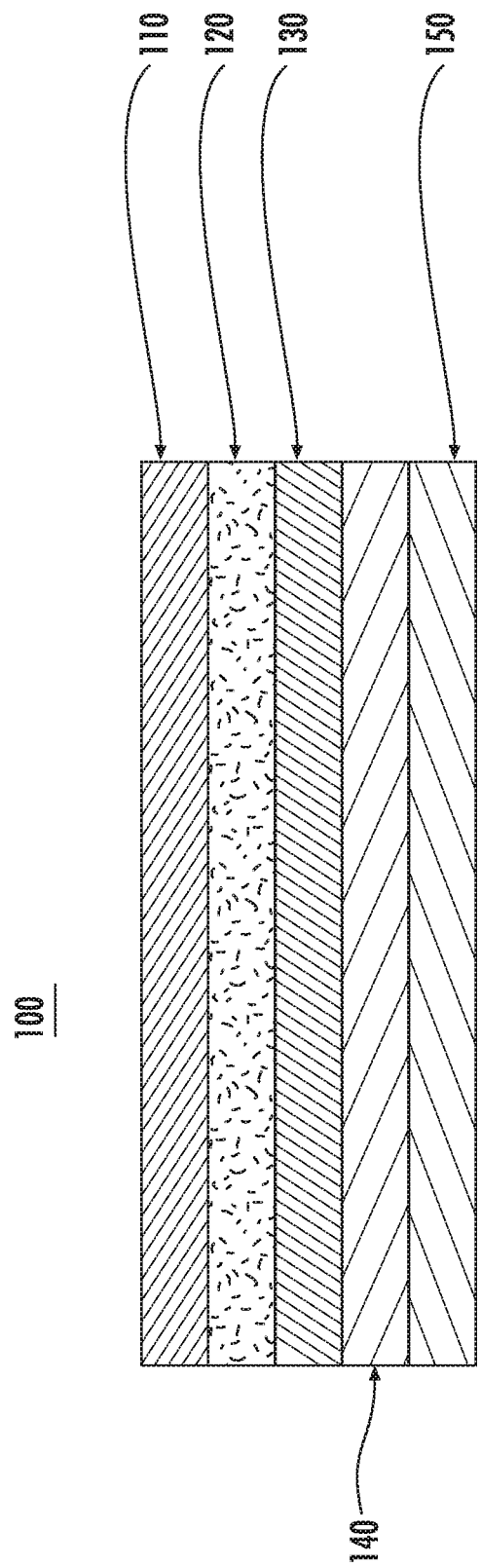

METHOD FOR MANUFACTURING A TRANSDERMAL DEVICE

TECHNICAL FIELD OF THE INVENTION

The present invention is directed to the field of transdermal patches, and specifically to a method for manufacturing a transdermal patch.

BACKGROUND OF THE INVENTION

Transdermal patches are drug delivery systems that typically include a backing material, a drug and an adhesive to adhere the patch to skin. Conventional uses include delivering a broad assortment of therapeutic agents, including nicotine and pain medications.

A typical conventional patch is shown in FIG. 1. Transdermal patch 100 includes backing layer 110 and drug-in-adhesive layer 120, may optionally also include rate controlling membrane 130 and adhesive layer 140 and other layers, as well. Regardless of the particular layering employed, these patches are typically sealed into pouches. To prevent the drug-in-adhesive layer 120 or the adhesive layer 140 from adhering to the pouch, the exposed drug-in-adhesive layer 120 or the exposed adhesive layer 140 of transdermal patch 100, as the case may be, is typically attached to an additional layer added, as illustrated in FIG. 1. The additional layer is strippable release liner 150. Release liner 150 prevents adherence of the exposed adhesive to surfaces during processing, prevents adherence to the primary package and allows patient handling of the patch prior to application to the patient's skin. The surface of release liner 150 attached to the adhesive has a special surface layer designed to release cleanly from the adhesive so that release liner 150 can easily be peeled from the adhesive by the patient without damage to the adhesive.

The conventional process for producing the prior art patches includes providing a spool of web material that is made up of such subsidiary layers as are desired. Web material moves along a conveyor to a cutting station, where generally rectangular cuts are made to form transdermal patches. These cuts are often referred to as "kiss cuts", in that unlike through-cuts, they extend only partially through the depth of the web material, typically through all the layers except for strippable release liner. Rectangular zones between transdermal patches are spaced a substantial distance from one another as shown, and define a waste material that, when removed, leaves behind a series of spaced apart rectangular islands that become transdermal patches as placed on skin.

The remaining web is then through-cut by vertical and horizontal lines 180 and then separated out into individual transdermal patches, each mounted to its supporting release liner. An arrangement of transdermal patch (its specific layers not shown) can be mated to a generally rectangular strippable release liner.

The substantial waste material that this process produces and then discards is very wasteful of the therapeutic agents that are at the heart of the transdermal patch.

A substantial fraction of the cost of a transdermal patch lies in the cost of the drug that it delivers. Known methods for manufacturing these patches begin with a continuous web that is a composite of the layers noted above, including the layer that carries the therapeutic agent, and the release liner film covering the exposed adhesive. The continuous web has indeterminate length, typically more than one thousand meters, and can have a width up to about one meter. This continuous web is converted to individual patches, the finished product, by punching the patch from the continuous web to the required size and shape and individually packaging the punched finished dosage, the patch, into a pouch. The longest dimension of the patch is much less than the width of the web so that many individual units are punched across the width. Punching of patches from this continuous web often results in significant losses of the drug due to spaces that may be required between the punched areas of the web. Because the layer that contains the drug is continuous, and because of losses of this layer in the process for punching the continuous web into individual dosages, an inefficient punching process can substantially increase production costs.

There remains a need for a method of manufacturing transdermal patches that more efficiently utilizes the therapeutic agents contained within the starting continuous web.

SUMMARY OF THE INVENTION

The present invention relates to a method of manufacturing a transdermal device from a continuous layered web which is conveyed linearly. Upper layers of the web can be kiss-cut along both horizontal lines, lengthwise down the web, and vertical lines, crosswise across the web. The lines can be cut down from a backing side of the transdermal device to the depth of the underlying strippable release liner, leaving the strippable release liner uncut and intact. Alternatively, the horizontal and vertical cuts can be through-cuts, which cut through all layers of the web. Several patterns of kiss-cuts and through-cuts, applied to the continuous web, are described.

Individual portions of the web are then peeled away from the liner of the starting web by machinery with a sharp edge that raises the front rim of the forward moving portion. For example, the individual portions can be a patch being generally rectangular in shape with rounded corners as defined by a punch employed to stamp the individual portions. The front rim of the individual portions then contacts a second web of strippable release liner that moves faster than the first web, resulting in transfer of the entire individual portions to the second web. As a continuous process applied to a line of contiguous patches, this results in a lateral spacing apart of the transdermal patches on this second web along the direction of movement of the second web. The patches in the second web may be through-cut without transfer to a new release liner yielding a finished product with the strippable release liner contiguous with the patch. While this process uses more release liner material, it conserves use of the more expensive drug bearing material. The rounded corners of the patch are cut during the process, as kiss-cuts, and the drug material filling the rounded corners is removed as waste. The rounded corners can be cut before or after the horizontal through-cuts down the length of the web.

In some cases, the vertical kiss-cut does not result in a clean separation of the contiguous patches, because the adjacent adhesive surfaces along the kiss-cut re-adhere after the kiss-cut. Each of lines can include a pair of lines leaving a thin strip of waste material between the patches. The thin strip is removed with the rounded corners leaving a narrow space between contiguous patches, preventing re-adherence between the contiguous patches. This process yields slightly more waste than the process with the single kiss-cut between the patches, but substantially reduces waste relative to the conventional process.

The process of the present invention provides a transdermal patch formed by efficient use of the drug-in-adhesive or other drug-carrying layer, thereby reducing waste of the most expensive portion of the transdermal patch.

The invention will be more fully described by reference to the following drawings.

BRIEF DESCRIPTION OF THE DRAWINGS

FIG. 1 is a cross-sectional view of a prior art web of starting material.

DETAILED DESCRIPTION OF THE INVENTION

Reference will now be made in greater detail to a preferred embodiment of the invention, an example of which is illustrated in the accompanying drawings. Wherever possible, the same reference numerals will be used throughout the drawings and the description to refer to the same or like parts.

The method for producing transdermal devices of the present invention includes providing layered web material. Starting web of layered web material is transported to cutting station 205 where it is through-cut along horizontal lines into separable strips, and kiss-cut along vertical lines down to the depth of the release liner. Portions where horizontal lines and vertical lines intersect can be cut out to provide rounded corners for zones of layered web material. For example, dies can be used to kiss-cut or punch out the portions. The portions can have a star or diamond-shaped so as to provide rounded corners for zones. Rounded corners can be cut before or after horizontal lines are made for horizontal through-cuts down the length of the web that form the separable strips.

Starting web can be cut into one or more separate webs, each made up of a series of adjoining segments that are delimited by vertical lines which can be kiss-cut. Each of segments will each include backing film layer, at least one drug-in-adhesive layer, and strippable release layer.

A web is moved along at a first average velocity (V1) in the direction of arrow A1 to transfer station where web faces web of release liner material. Web of release liner material moves at a second average velocity (V2). Second average velocity (V2) is greater than first average velocity (V1). Transfer machinery detaches segments from release layer and affixes the detached segments to release liner material which is faster moving. Transfer machinery can accomplish the transfer using a sharp edge on the machinery that raises the front rim of the forward moving segment. Front rim then contacts web of release liner that moves faster than web. Front rim then adheres to web of release liner resulting in transfer of segment to web of release liner. Web of release liner is sufficiently wider to provide a broader base in the direction orthogonal to its direction of transfer, and its faster movement with respect to web results in a desired level of lateral spacing, so that web of release liner can then be cut to form patch. Patch can be a transdermal patch including film layer, at least one drug-in-adhesive layer and release liner. Alternatively, web of release liner can be the same width as patch, yielding a finished product with no extension of release liner at the sides of patch.

In some cases, the vertical kiss-cut does not result in a clean separation of the contiguous patches, because the adjacent adhesive surfaces along the kiss-cut re-adhere after the kiss-cut. An embodiment in which horizontal lines and vertical lines include a pair of horizontal lines and vertical lines leaving a thin strip of waste material between the patches. Thin strip is removed with the rounded corners leaving a narrow space between contiguous patches, preventing re-adherence between the contiguous patches.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A method for manufacturing an individual transdermal patch comprising the steps of:
   providing a first web of material, the first web of material including a film layer, at least one drug-in-adhesive layer and a first release liner;
   cutting a plurality of vertical lines and horizontal lines in the first web of material to delimit a plurality of segments of the first web of material;
   cutting out areas of the first web of material where the first web is through-cut along horizontal lines into separable strips and kiss-cut along vertical lines down to the depth of the first release liner, the areas where the horizontal and vertical line intersect are cut out in a portion having a star shape to provide rounded corners for the plurality of segments of the first web material to delimit the plurality of segments of the first web of material;
   peeling away portions of the first release liner from the plurality of segments of the first web material; and
   transferring the plurality of segments of the first web material beneath the peeled away portions of the first release liner to a second web of a release liner, the first web of material is moved along at a first average velocity (V1) to a transfer station where the first web of material faces the second web of the release liner material and the second web of the release liner material moves at a second average velocity (V2), the second average velocity (V2) is greater than first average velocity (V1) to provide a predetermined spacing of the transferred plurality of segments on the second web of the release layer,
   wherein the transferred plurality of segments each comprise the individual transdermal patch and wherein the step of cutting out areas of the first web further comprises cutting a piece of the first web down to a depth of the first release liner by kiss-cut to provide a strip between adjacent transdermal patches and removing the strip leaving between adjacent transdermal devices a space to facilitate the removal of the transdermal patch and transfer from the first web (V1) moving at first web velocity to the second web moving at the second web velocity (V2).

2. The method of claim 1 wherein the step of cutting out areas of the first web is performed by stamping.

3. The method of claim 1 further comprising the step of cutting the transferred plurality of segments apart.

4. The method of claim 1 wherein a front rim of the first web of material contacts the second web of the release liner and the front rim then adheres to the second web of the release liner resulting in transfer of the segment of the first web material beneath the peeled away portion of the first release liner to the second web of the release liner.

5. The method of claim 4 wherein the second web of the release liner is wider than the width of the transferred plurality of segments.

6. The method of claim 4 wherein the second web of the release liner has a width which is substantially the same as the width of the transferred plurality of segments.

7. The method of claim 1 wherein each of the plurality of vertical lines and the plurality of horizontal lines are a pair of lines.

\* \* \* \* \*